(12) United States Patent
Kim et al.

(10) Patent No.: US 8,500,646 B2
(45) Date of Patent: Aug. 6, 2013

(54) COLOR DOPPLER MODE IMAGE PROCESSING IN AN ULTRASOUND SYSTEM

(75) Inventors: Baek Sop Kim, Chuncheon-si (KR); Hyeong Do Lee, Seoul (KR)

(73) Assignee: Medison Co., Ltd., Kangwon-Do (KR)

( * ) Notice: Subject to any disclaimer, the term of this patent is extended or adjusted under 35 U.S.C. 154(b) by 519 days.

(21) Appl. No.: 12/767,300

(22) Filed: Apr. 26, 2010

(65) Prior Publication Data

US 2010/0280383 A1 Nov. 4, 2010

(30) Foreign Application Priority Data

Apr. 30, 2009 (KR) .................. 10-2009-0038474

(51) Int. Cl.
*A61B 8/00* (2006.01)
(52) U.S. Cl.
USPC ........................ 600/453; 600/437; 600/454
(58) Field of Classification Search
USPC ........................................................ 600/453
See application file for complete search history.

(56) References Cited

U.S. PATENT DOCUMENTS

| | | | |
|---|---|---|---|
| 5,860,929 A | 1/1999 | Rubin et al. | |
| 6,217,520 B1 | 4/2001 | He et al. | |
| 6,352,509 B1 * | 3/2002 | Kawagishi et al. | 600/443 |
| 2003/0181814 A1 * | 9/2003 | Ji et al. | 600/453 |
| 2004/0138567 A1 | 7/2004 | Ito et al. | |
| 2006/0116582 A1 | 6/2006 | Yoshida et al. | |

FOREIGN PATENT DOCUMENTS

| | | |
|---|---|---|
| EP | 0 871 043 A2 | 10/1998 |
| JP | 2004-033732 | 2/2004 |
| JP | 2008-154891 | 7/2008 |
| JP | 2008-154891 | * 10/2008 |

OTHER PUBLICATIONS

Extended Search Report for EP 10160682.0-2220, Mailed Jul. 28, 2010, 6 pages.

* cited by examiner

*Primary Examiner* — Tse Chen
*Assistant Examiner* — Patricia Park
(74) *Attorney, Agent, or Firm* — McDermott Will & Emery LLP (57) ABSTRACT

Embodiments for processing a color Doppler mode image in an ultrasound system are disclosed. In one embodiment, the ultrasound system includes: a Doppler signal acquisition unit configured to transmit and receive ultrasound signals to and from a target object to acquire first Doppler signals; and a processing unit configured to form color Doppler mode images including power images and velocity images and a mask for detecting a region of interest by using the color Doppler mode images, the processing unit being further configured to mask the power images and the velocity image by using the mask.

17 Claims, 6 Drawing Sheets

| 0 | 0 | 0 | 0 | 0 | 0 | 0 | 0 |
|---|---|---|---|---|---|---|---|
| 0 | 1 | 1 | 1 | 1 | 1 | 1 | 0 |
| 0 | 1 | 2 | 2 | 2 | 2 | 1 | 0 |
| 0 | 1 | 2 | 3 | 3 | 2 | 1 | 0 |
| 0 | 1 | 2 | 2 | 2 | 2 | 1 | 0 |
| 0 | 1 | 1 | 1 | 1 | 1 | 1 | 0 |
| 0 | 0 | 0 | 0 | 0 | 0 | 0 | 0 |

COLOR DOPPLER MODE IMAGE PROCESSING IN AN ULTRASOUND SYSTEM

CROSS-REFERENCE TO RELATED APPLICATIONS

The present application claims priority from Korean Patent Application No. 10-2009-0038474 filed on Apr. 30, 2009, the entire subject matter of which is incorporated herein by reference.

TECHNICAL FIELD

The present disclosure relates to ultrasound image processing, and more particularly to color Doppler mode image processing in an ultrasound system.

BACKGROUND

Recently, an ultrasound system has been extensively used in the medical field due to its non-invasive and non-destructive nature. Modern high-performance ultrasound imaging diagnostic systems and techniques are typically used to produce two- or three-dimensional ultrasound images of internal features of patients. To provide the ultrasound images, the ultrasound system operates in various image modes such as a brightness mode, a Doppler mode and the like to acquire ultrasound images for diagnosis.

In the Doppler mode, the ultrasound system provides a color Doppler mode image visualizing velocities of moving objects such as blood flow, heart, etc. The color Doppler mode image includes a power image visualizing powers of Doppler signals as 2-dimensional distribution and a velocity image visualizing velocities of the moving objects, which may be computed from the Doppler signals, as 2-dimensional distribution. The color Doppler mode image may visualize the blood flow in real time in a wide range from the blood flow of a high velocity in a large vessel to the blood flow of a low velocity in a small vessel.

Conventionally, smoothing has been carried out upon the velocity image for enhancement. However, since the blood flow on the velocity image may be extended to the vessel region due to the smoothing, bleeding, which shows blood escape from the real vessel on the velocity image, may be caused. Further, a loss of small vessels may occur. Also, the connectivity loss, i.e., portions of vessel are cut in the velocity image, may be generated. The peaks of the blood flow may be important clinical information in the velocity image. However, the peak loss, i.e., peaks of the blood flow are disappeared in the velocity image, may be also generated due to the smoothing thereupon.

Further, the effectiveness of pixels in the power image is determined through the fixed thresholding method. However, since the power of blood flow varies according to the heartbeat, the vascular collapse, i.e., the blood vessel region is collapsed in the power image, may occur.

SUMMARY

Embodiments for processing a color Doppler mode image in an ultrasound system are provided. The ultrasound system comprises: a Doppler signal acquisition unit configured to transmit and receive ultrasound signals to and from a target object to acquire first Doppler signals; and a processing unit configured to form color Doppler mode images including power images and velocity images and a mask for detecting a region of interest by using the color Doppler mode images, the processing unit being further configured to mask the power images and the velocity image by using the mask.

In another embodiment, a method of processing a color Doppler mode image in an ultrasound system including a Doppler signal acquisition unit and a processing unit, comprises: a) at the Doppler signal acquisition unit, transmitting and receiving ultrasound signals to and from a target object to acquire first Doppler signals; b) at the processing unit, forming color Doppler mode images including power images and velocity images; c) at the processing unit, forming a mask for detecting a region of interest by using the color Doppler mode images; and d) at the processing unit, masking the power images and the velocity image by using the mask.

In another embodiment, a computer readable medium comprises computer executable instructions that may be configured to perform the following acts: a) transmitting and receiving ultrasound signals to and from a target object to acquire first Doppler signals; b) forming color Doppler mode images including power images and velocity images; c) forming a mask for detecting a region of interest by using the color Doppler mode images; and d) masking the power images and the velocity image by using the mask.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
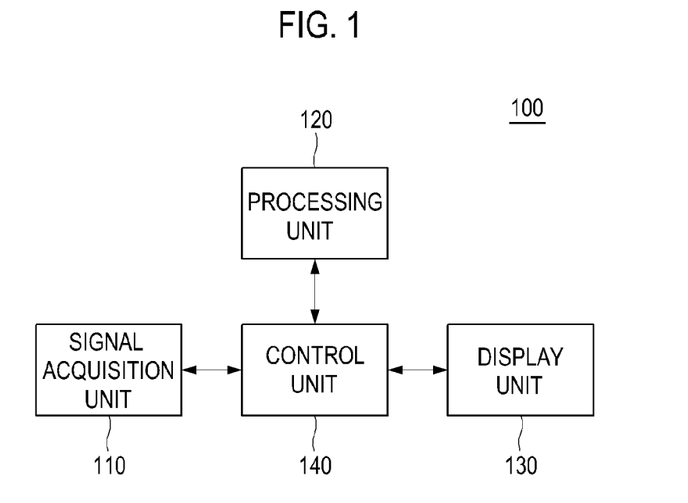
FIG. 1 is a block diagram showing an illustrative embodiment of an ultrasound system.

Referring to FIG. 1, an illustrative embodiment of an ultrasound system 100 is shown. As depicted therein, the ultrasound system 100 may include a signal acquisition unit 110. The signal acquisition unit 110 may be operable to alternately transmit and receive ultrasound signals to and from a moving target object (e.g., heart, blood flow, etc). The signal acquisition unit 110 may acquire Doppler signals corresponding to a plurality of frames based on the received ultrasound signals. In one embodiment, the frames may include color Doppler mode image frames.

Figure 2:
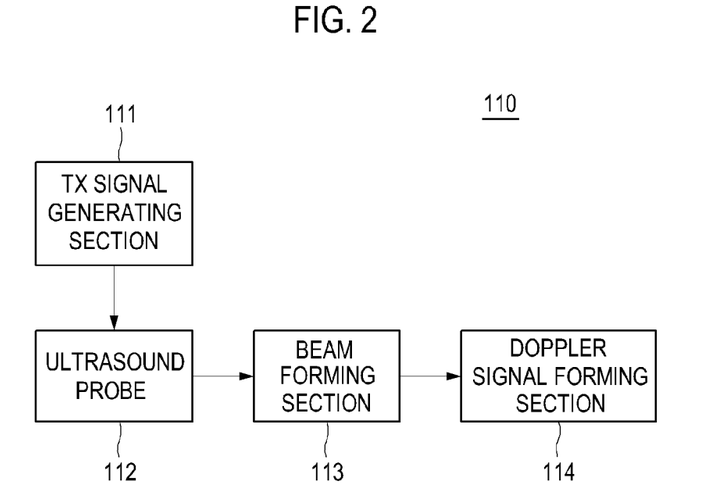
FIG. 2 is a block diagram showing an illustrative embodiment of a signal acquisition unit in FIG. 1.

FIG. 2 is a block diagram showing an illustrative embodiment of the signal acquisition unit 110 in FIG. 1. Referring to FIG. 2, the signal acquisition unit 110 may include a transmit (Tx) signal generating section 111. The Tx signal generating section 111 may be operable to generate a plurality of transmit signals.

The signal acquisition unit 110 may further include an ultrasound probe 112 containing a plurality of transducer elements for reciprocally converting ultrasound signals and electrical signals. The ultrasound probe 122 may be operable to transmit ultrasound signals into a target object in response to the transmit signals. The ultrasound probe 112 may be further operable to receive echo signals reflected from the target object to thereby output electrical receive signals, which are analog signals. The transmission and reception of the ultrasound signals are alternately carried out to output a plurality of electrical receive signals.

The signal acquisition unit 110 may further include a beam forming section 113. The beam forming section 113 may be operable to convert the electrical receive signals into digital signals. The beam forming section 113 may be further operable to apply delays to the digital signals in consideration of distances between the elements and focal points, thereby outputting digital receive-focused signals.

The signal acquisition unit 110 may further include a Doppler signal forming section 124 that may be operable to form Doppler signals based on the digital receive-focused signals. The Doppler signals may contain power information and velocity information. The Doppler forming section 124 may be operable to perform signal processing (e.g., gain adjustment, filtering and the like) necessary for forming the Doppler signals upon the digital receive-focused signals.

The ultrasound system 100 may further include a processing unit 120 coupled to the signal acquisition unit 110. The processing unit 120 may be operable to form a color Doppler mode image based on the Doppler signals provided from the signal acquisition unit 110. The processing unit 120 may be further operable to form a mask for detecting a blood vessel region by using the color Doppler mode image and perform masking upon the color Doppler mode image. The color Doppler mode image may include a power image indicative of powers of the Doppler signals as 2-dimensional distribution and a velocity image indicative of velocities of the Doppler signals as 2-dimensional distribution.

Figure 3:
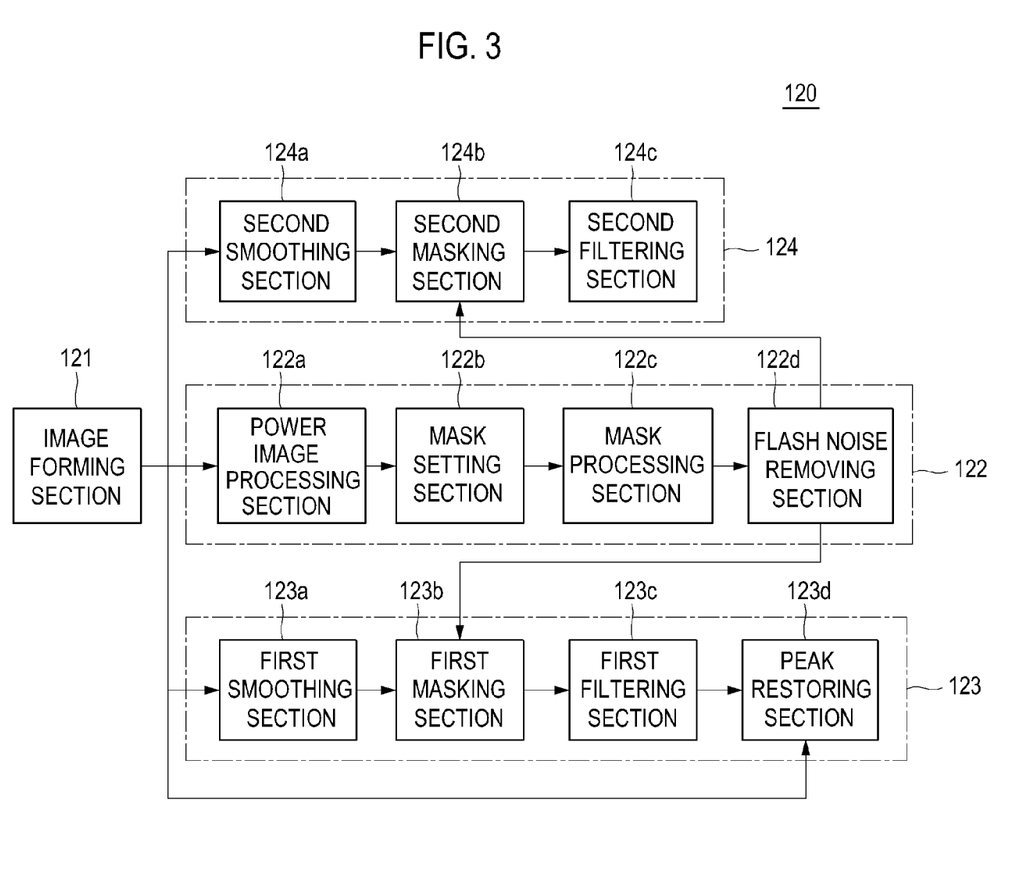
FIG. 3 is a block diagram showing an illustrative embodiment of a processing unit in FIG. 1.

FIG. 3 is a block diagram showing an illustrative embodiment of the processing unit. Referring to FIG. 3, the processing unit 120 may include an image forming section 121, a mask forming section 122, a first image processing section 123 and a second image processing section 124.

The image forming section 121 may be operable to form a power image and a velocity image based on the Doppler signals provided from the signal acquisition unit 110. The mask forming section 122 may be operable to form a mask for detecting a blood vessel region, which is a region of interest, on the power image. In one embodiment, the mask forming section 122 may include a power image processing section 122a, a mask setting section 122b, a mask processing section 122c and a flash noise removing section 122d.

The power image processing section 122a may be operable to analyze the power images sequentially provided from the image forming section 121 to set a reference power image. In one embodiment, a power image having a mean power greater than a predetermined threshold may be set as the reference power image. The power image processing section 122a may be further operable to compound power images, of which mean powers are less than the predetermined threshold, with the reference power image to thereby form compound images.

Figure 4:
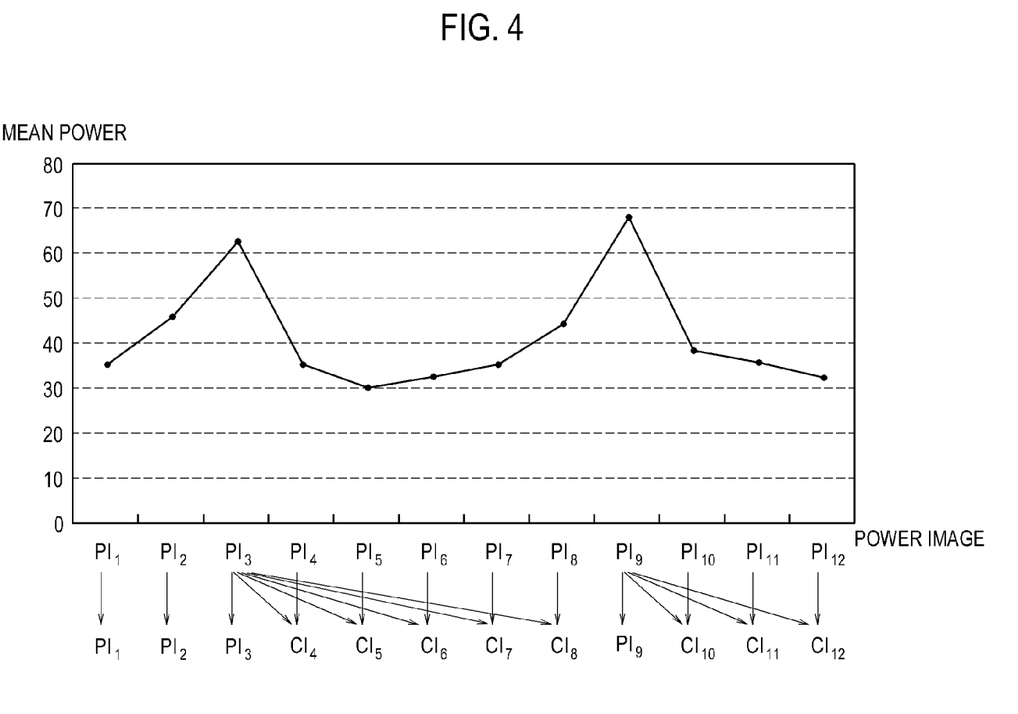
FIG. 4 is an exemplary diagram showing an example of a graph of mean powers for power images and formation of compound images.

FIG. 4 shows an example of mean powers of the power images and examples of setting the reference power image to form the compound images by using the power images. Referring to FIG. 4, if a first power image $PI_1$ is provided, then the power image processing section 122a may be operable to compute a mean power of the first power image (hereinafter, referred to as "first mean power"). The power image processing section 122a may initially set the first power image $PI_1$ and the first mean power as the reference power image and the reference mean power.

If a second power image $PI_2$ is provided from the image forming section 121, then the power image processing section 122a may be operable to compute the mean power of the second power image $PI_2$ (hereinafter, referred to as "second mean power"). The power image processing section 122a may check whether the second mean power is greater than the predetermined threshold (e.g., reference mean power ×0.8). If the second mean power is greater than the predetermined threshold, then the power image processing section 122a may be operable to set the second power image $PI_2$ as a new reference power image.

If a third power image $PI_3$ is provided from the image forming section 121, then the power image processing 122a may be operable to compute the mean power of the third power image $PI_3$ (hereinafter, referred to as "third mean power"). The power image processing section 112a may check whether the third mean power is greater than the predetermined threshold (e.g., reference mean power ×0.8). If the third mean power is greater than the predetermined threshold, then the power image processing section 122a may be operable to set the third power image $PI_3$ as a new reference power image.

If a fourth power image $PI_4$ is provided from the image forming section 121, then the power image processing 122a may be operable to compute the mean power of the fourth power image $PI_4$ (hereinafter, referred to as "fourth mean power"). The power image processing section 122a may check whether the fourth mean power is greater than the predetermined threshold (e.g., reference mean power ×0.8). If the fourth mean power is less than the predetermined threshold, then the power image processing section 122a may be operable to compound the fourth power image $PI_4$ and the reference power image, thereby forming a compound image $CI_4$. In one embodiment, since the power image having relatively low mean power is compounded with the reference power image, it may be prevented that the blood vessel region is indicated as a small region on the power image due to the low mean power.

If fifth to eighth power images $PI_5$-$PI_8$ are provided from the image forming section 121, then the power image processing 122a may be operable to compute mean powers of the fifth to eighth power images $PI_5$-$PI_8$ (hereinafter, referred to as "fifth to eighth mean powers"). The power image processing section 112a may compare the fifth to eighth mean powers with the predetermined threshold (e.g., reference mean power ×0.8). If the fifth to eighth mean powers are less than the predetermined threshold, then the power image processing section 122a may be operable to compound the respective fifth to eighth power images $PI_5$-$PI_8$ with the reference power image.

If a ninth power image $PI_9$ is provided from the image forming section 121, then the power image processing 122a may be operable to compute the mean power of the ninth power image $PI_9$ (hereinafter, referred to as "ninth mean power"). The power image processing section 112a may check whether the ninth mean power is greater than the predetermined threshold (e.g., reference mean power ×0.8). If the ninth mean power is greater than the predetermined threshold, then the power image processing section 122a may be operable to set the ninth power image $PI_9$ as a new reference power image.

If tenth to twelfth power images $PI_{10}$-$PI_{12}$ are provided from the image forming section 121, then the power image processing 122a may be operable to compute mean powers of the tenth to twelfth power images $PI_{10}$-$PI_{12}$ (hereinafter, referred to as "tenth to twelfth mean powers"). The power image processing section 122a may compare each of the tenth to twelfth mean powers with the predetermined threshold (e.g., reference mean power ×0.8). If the tenth to twelfth mean powers are less than the predetermined threshold, then the power image processing section 122a may be operable to compound each of the tenth to twelfth power images $PI_{10}$-$PI_{12}$ with the reference power image $PI_9$, thereby forming compound images $CI_{10}$-$CI_{12}$.

Figure 5A:
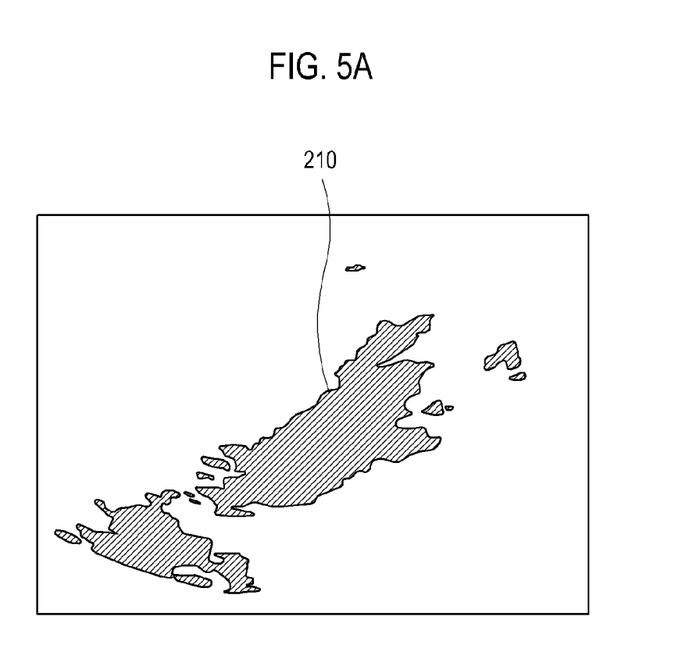
FIG. 5A is a diagram showing an example of setting a mask.

The mask setting section 122b may be operable to set a region of interest, i.e., a mask for detecting a blood vessel region on each of the reference power images $PI_1$-$PI_3$ and $PI_9$ and the compound images $CI_4$-$CI_8$ and $CI_{10}$-$CI_{12}$, as shown in FIG. 5A. The mask may include one or more sub regions. In one embodiment, the mask may be set by using various well-known methods, such as a thresholding method, an area expanding method, an area segmenting method, a contour extracting method, a graph method, a watershed method, and the like.

Figure 5B:
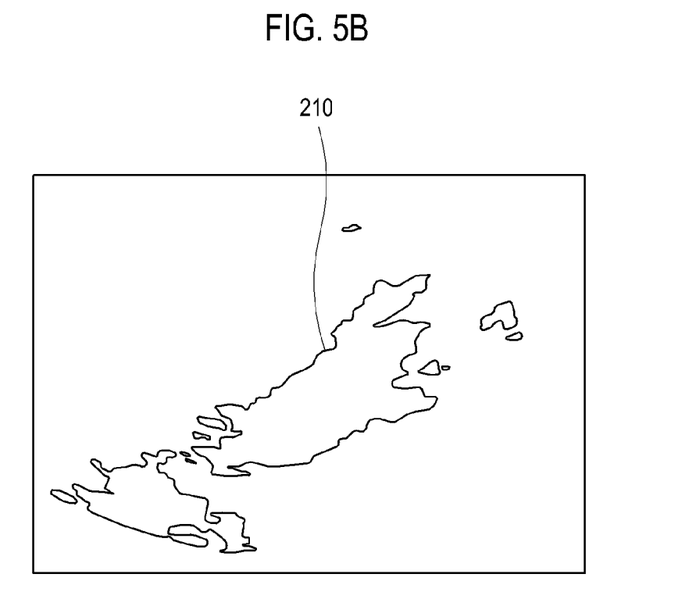
FIG. 5B is a diagram showing an example of detecting contours of a mask.
Figure 5C:
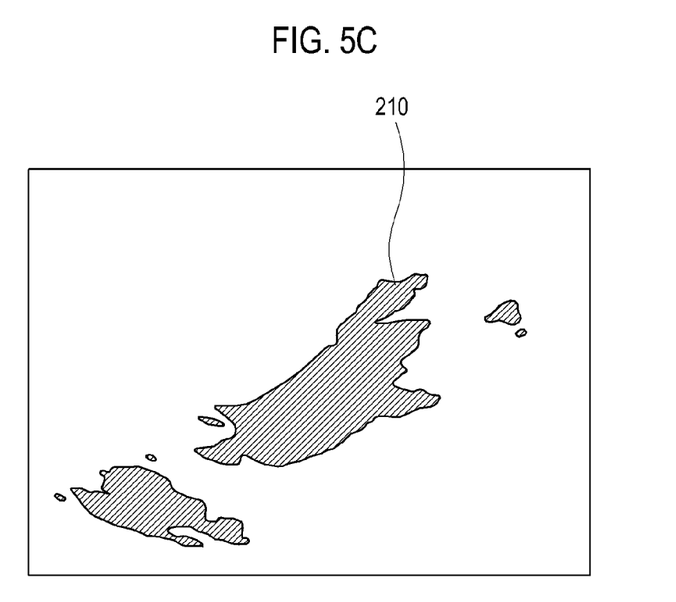
FIG. 5C is a diagram showing an example of smoothed contours of a mask.
Figure 5D:
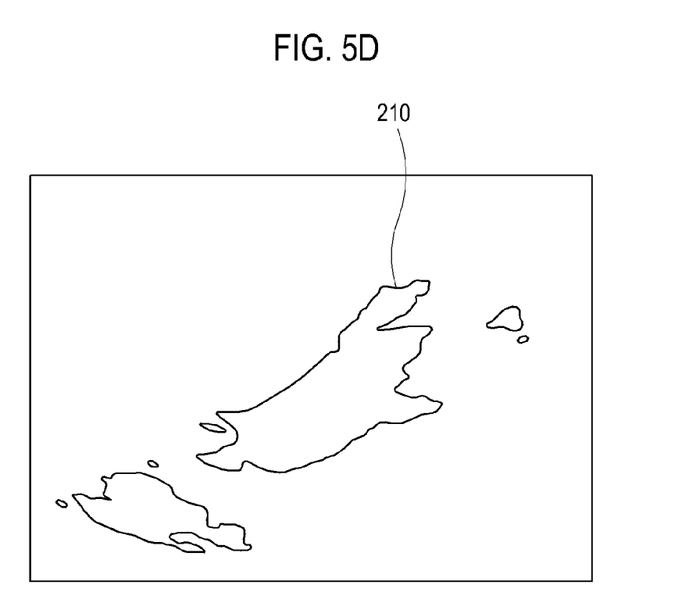
FIG. 5D is a diagram showing an example resulting from performing filling upon a mask.

The mask processing section 122c may be operable to detect contours of the mask set in the mask setting section 122b, as illustrated in FIG. 5B. In one embodiment, by way of non-limiting example, the contours may be detected by using contour following, mathematical morphological operation and the like. The mask processing section 122c may be operable to perform smoothing upon the detected contours of the mask, as shown in FIG. 5C. The smoothing may be performed through at least one of Fourier descriptor based algorithm, chain codes, active contour and the like. The mask processing section 122c may be further operable to perform filling upon the smoothed mask, as shown in FIG. 5D.

The flash noise removing section 122d may be operable to remove flash noises from the mask provided from the mask processing section 122c. The flash noises may occur due to muscles neighboring to the blood vessels, heart muscles and the like whose moving velocities are slower than those of the blood flows while their moving powers are greater than those of the blood flows. The flash noises may be appeared and disappeared in a flash. In one embodiment, the flash noise removing section 122d may be operable to perform region labeling upon the mask of the frame (reference power image or compound image) to assign a specific index to each of the sub regions in the mask. The flash noise removing section 122d may compare the mask of the current frame with the masks of the predetermined number of the previous frames (e.g., 3 frames). If the indices in the mask of the current frame are not identical to those of the respective sub regions of the predetermined number of the previous frames, then the flash noise removing section 122d may determine the different indexed sub region(s) in the mask of the current frame as the flash noises to thereby remove them. In another embodiment, the flash noise removing section 122d may check whether each of the sub regions in the mask is effective as the blood vessel. The flash noise removing section 122d may remove the sub regions, which do not have the effective values. The effectiveness may be determined by checking whether the maximum value of pixels in each sub region in the mask is greater than a predetermined value. When the maximum value of pixels in the sub region is less than the predetermined value, the corresponding region sub may be determined as the noise. Also, the effectiveness may be determined by checking whether the contours of the sub regions in the mask are flat over a predetermined portion.

The first image processing section 123 may use the mask provided from the mask forming section 122 to mask the velocity images, which may be sequentially provided from the image forming section 121. Referring to FIG. 3, the first image processing section 123 may include a first smoothing section 123a, a first masking section 123b, a first filtering section 123c and a peak restoring section 123d.

The first smoothing section 123a may be operable to perform smoothing upon the velocity images. In one embodiment, by way of non-limiting example, the smoothing may be carried out through one of the mean filtering, Gaussian filtering, median filtering, low pass filtering, graph regularization and the like.

The first masking section 123b may use the mask provided from the mask forming section 122 to mask the smoothed velocity images. The first masking section 123b may be operable to use the mask to set regions corresponding to the blood vessels for each of pixels of the respective velocity images as "1" and regions except for the blood vessel regions as "0."

Figure 6:
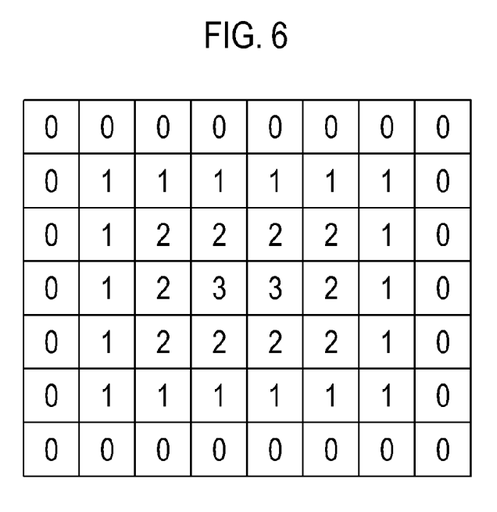
FIG. 6 is a diagram showing an example of a distance transform image.

The first filtering section 123c may be operable to apply distance weighting to the masked velocity images and then perform border smoothing thereupon. The distance weighting may be performed such that the velocities of the blood flow at blood vessel border portions are indicated slower than those at the center portion of the blood flow. The first filtering section 123c may be operable to form distance transform images by using the masked velocity images. The first filtering section 123c may set pixels corresponding to background (i.e., not blood vessel regions) as "0" and the rest of the pixels as minimum distance values from the background, as shown in FIG. 6, to thereby form the distance transform images. Distance weighting corresponding to the pixels of the distance transform image may be expressed as a function of the pixels. In one embodiment, the distance weighting may be defined as w(i)=min (i*0.2+0.6, 1), wherein i represents a pixel value in the distance transform image. Thus, if a pixel value of the smoothed velocity image is f(x, y), this pixel value may be transformed to f(x, y)*w(f(x, y)). The first filtering section 123c may be further operable to detect blood vessel border portion in the distance weighted velocity image and then perform smoothing upon the detected border portions.

The peak restoring section 123d may be operable to restore peaks in the velocity images provided from the first filtering section 123c. The maximum velocity (i.e., peak) of the blood flow in the blood vessel may provide clinically important information, so that the peaks should be maintained. However, the peaks may be blurred during the smoothing, which makes the peak values lowered. Thus, the peak restoring section 123d may be operable to compute image differences between the velocity images provided from the image processing section 121 and the smoothed velocity images to thereby obtain a difference image. The peak restoring section 123d may check peak candidates, which are regions over the image difference of "0" on the difference image and then detect regions greater than a predetermined threshold as the peak regions among the peak candidates. The peak restoring section 123d may be operable to restore the peaks in the smoothed velocity image by using the detected peak regions.

The second image processing section 124 may be operable to use the mask provided from the mask forming section 122 to mask the power images sequentially provided from the image forming section 121. In one embodiment, the second image processing section 124 may include a second smoothing section 124a, a second masking section 124b and a second filtering section 124c.

If the power images are provided from the image forming section 121, the second smoothing section 124a may be operable to perform smoothing upon the power images. In one embodiment, the smoothing may be performed through mean filtering, Gaussian filtering, median filtering, low pass filtering, graph regularization and the like.

The second masking section 124b may use the mask provided from the mask forming section 122 to mask the smoothed power images. The second masking section 124b may be operable to use the mask to set regions corresponding to the blood vessels for each of pixels of the respective power images as "1" and regions except for the blood vessel regions as "0."

The second filtering section 124c may be operable to apply distance weighting to the masked power image and then perform border smoothing thereupon. The distance weighting may be performed such that the powers of the blood flow at blood vessel border portions are indicated lower than those at the center portion of the blood flow. The second filtering section 124c may be operable to form distance transform images by using the masked power images. The second filtering section 124c may be further operable to detect blood vessel border portion in the distance weighted power images and then perform smoothing upon the detected border portions.

Referring back to FIG. 1, the display unit 130 may include at least one of a CRT monitor, a LCD monitor, a plate display and the like. The display unit 130 may display the color Doppler mode images formed in the processing unit 120, i.e., velocity images and power images. The control unit 140 may operable to control the formation, image processing and display of the power images and the velocity images.

In another embodiment, instructions for performing the above method of processing the color Doppler mode image may be recorded in a computer readable medium using computer-readable instructions. The computer readable medium may include any types of record media, which can be read by a computer system. The computer readable medium may include read only memory (ROM), random access memory (RAM), CD-ROM, magnetic tape, floppy disk, optical-data recording apparatus and the like. The computer readable medium comprises computer executable instructions that may be configured to perform the following acts: a) transmitting and receiving ultrasound signals to and from a target object to acquire first Doppler signals; b) forming color Doppler mode images including power images and velocity images; c) forming a mask for detecting a region of interest by using the color Doppler mode images; and d) masking the power images and the velocity image by using the mask.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a signal acquisition unit configured to transmit and receive ultrasound signals to and from a target object to acquire first Doppler signals; and
   a processing unit configured to form color Doppler mode images including power images and velocity images, to analyze the power images to set a references power image whose mean power is greater than a predetermined threshold, to compound the reference power image with power images whose mean power is less than the predetermined threshold to form compound images, to set a mask for detecting a region of interest by using the reference power image and the compound images, and to detect contours of the mask, to perform smoothing upon the detected contours, and to perform filling upon the smoothed mask, the processing unit being further configured to mask the power images and the velocity images by using the mask.

2. The ultrasound system of claim 1, wherein the processing unit includes:
   an image forming section configured to form the power images and the velocity images;
   a mask forming section configured to form a mask by using the power image;
   a first image processing section configured to mask the velocity images by using the mask; and
   a second image processing section configured to mask the power images by using the mask.

3. The ultrasound system of claim 2, wherein the mask forming section includes:
   a power image processing section configured to analyze the power images to set the reference power image whose mean power is greater than the predetermined threshold, and to compound the reference power image with power images whose mean power is less than the predetermined threshold to form the compound images;
   a mask setting section configured to set the mask for detecting the region of interest by using the reference power image and the compound images; and
   a mask processing section configured to detect the contours of the mask, perform the smoothing upon the detected contours, and perform the filling upon the smoothed mask.

4. The ultrasound system of claim 3, wherein the predetermined threshold is a value obtained by multiplying the reference mean power by a predetermined value.

5. The ultrasound system of claim 4, wherein the mask forming section includes a flash noise removing section to remove flash noises in the mask.

6. The ultrasound system of claim 4, wherein the power image processing section is configured to:
   compute a first mean power of a first power image provided from the image forming section to set a reference mean power;
   set the first power image as a reference power image;
   compute an $i^{th}$ mean power of an $i^{th}$ power image provided from the image processing section, wherein i is a positive integer greater than 1;
   compare the $i^{th}$ power with a predetermined threshold;
   set, when the $i^{th}$ mean power is greater than the predetermined threshold, the $i^{th}$ mean power as a new reference mean power and set the $i^{th}$ power image as a new reference power image; and compound, when the $i^{th}$ mean power is less than the predetermined threshold, the $i^{th}$ power image to the reference power image.

7. The ultrasound system of claim 2, wherein the first image processing section includes:
   a first smoothing section configured to perform smoothing upon the velocity images;
   a first masking section configured to mask the smoothed velocity images by using the mask;
   a first filtering section configured to perform distance weighting and border smoothing upon the masked velocity images; and
   a peak restoring section configured to compute image differences between the velocity image provided from the image processing section and the distance-weighted and border-smoothed velocity images to obtain a difference image, detect peak regions by using the difference image, and restore peaks of the distance-weighted and border-smoothed velocity images by using the detected peak regions.

8. The ultrasound system of claim 2, wherein the second image processing section includes:
   a second smoothing section configured to perform smoothing upon the power images;
   a second masking section configured to mask the smoothed power images; and
   a second filtering section configured to perform distance weighting and border smoothing upon the masked power images.

9. The ultrasound system of claim 1, further include a display unit to display the power images and the velocity images.

10. A method of processing a color Doppler mode image in an ultrasound system including a Doppler signal acquisition unit and a processing unit, comprising:
    a) at the Doppler signal acquisition unit, transmitting and receiving ultrasound signals to and from a target object to acquire first Doppler signals;
    b) at the processing unit, forming color Doppler mode images including power images and velocity images;
    c) at the processing unit, forming a mask for detecting a region of interest by using the power images, wherein the c) includes:
       c1) analyzing the power images to set a reference power image whose mean power is greater than a predetermined threshold, and compounding the reference power image with power images whose mean power is less than the predetermined threshold to form compound images;
       c2) setting the mask for detecting the region of interest by using the reference power image and the compound images; and
       c3) detect contours of the mask to perform smoothing upon the detected contours; and
       c4) performing filling upon the smoothed mask; and
    d) at the processing unit, masking the power images and the velocity image by using the mask.

11. The method of claim 10, wherein the c) further includes removing flash noises from the mask.

12. The method of claim 10, wherein the predetermined threshold is a value obtained by multiplying the reference mean power by a predetermined value.

13. The method of claim 10, wherein the c1) includes:
    computing a first mean power of a first power image provided from the image forming section to set a reference mean power;
    setting the first power image as a reference power image;
    computing an $i^{th}$ mean power of an $i^{th}$ power image provided from the image processing section, wherein i is a positive integer greater than 1;
    comparing the $i^{th}$ mean power with a predetermined threshold;
    setting, when the $i^{th}$ mean power is greater than the predetermined threshold, the $i^{th}$ mean power as a new reference mean power and set the $i^{th}$ power image as a new reference power image; and
    compounding, when the $i^{th}$ mean power is less than the predetermined threshold, the $i^{th}$ power image to the reference power image.

14. The method of claim 10, wherein the d) includes:
    performing smoothing upon the velocity images;
    masking the smoothed velocity images by using the mask;
    performing distance weighting and border smoothing upon the masked velocity images;
    computing image differences between the velocity image provided from the image processing section and the distance-weighted and border-smoothed velocity images to obtain a difference image;
    detecting peak regions by using the difference image; and
    restoring peaks of the distance-weighted and border smoothed velocity images by using the detected peak regions.

15. The method of claim 10, wherein the d) include:
    performing smoothing upon the power images;
    masking the smoothed power images; and
    performing distance weighting and border smoothing upon the masked power images.

16. The method of claim 10, further include displaying the power images and the velocity images.

17. A non-transitory computer readable medium comprising computer executable instructions configured to perform following acts:
    a) transmitting and receiving ultrasound signals to and from a target object to acquire first Doppler signals;
    b) forming color Doppler mode images including power images and velocity images;
    c) forming a mask for detecting a region of interest by using the power images the c) includes:
       c1) analyzing the power images to set a reference power image whose mean power is greater than a predetermined threshold, and compounding the reference power image with power images whose mean power is less than the predetermined threshold to form compound images;
       c2) setting the mask for detecting the region of interest by using the reference power image and the compound images; and
       c3) detect contours of the mask to perform smoothing upon the detected contours; and
       c4) performing filling upon the smoothed mask; and
    d) masking the power images and the velocity image by using the mask.

* * * * *